(12) United States Patent
Sokolov

(10) Patent No.: US 7,095,820 B2
(45) Date of Patent: Aug. 22, 2006

(54) METHOD AND AN APPARATUS FOR EXAMINING AN OBJECT BY USING IONIZING RADIATION

(75) Inventor: Skiff Sokolov, Lidingö (SE)

(73) Assignee: Xcounter AB, Danderyd (SE)

( * ) Notice: Subject to any disclaimer, the term of this patent is extended or adjusted under 35 U.S.C. 154(b) by 594 days.

(21) Appl. No.: 10/357,399

(22) Filed: Feb. 4, 2003

(65) Prior Publication Data

US 2004/0136492 A1 Jul. 15, 2004

(30) Foreign Application Priority Data

Jan. 10, 2003 (SE) ............................................. 0300030

(51) Int. Cl.
*G01N 23/201* (2006.01)

(52) U.S. Cl. .......................... 378/86; 250/358.1; 378/19
(58) Field of Classification Search ...................... 378/4, 378/19, 70, 82, 86, 87; 250/370.08, 370.09, 250/370.1, 306, 307, 308, 309, 310, 311, 250/358.1, 336.1
See application file for complete search history.

(56) References Cited

U.S. PATENT DOCUMENTS 4,598,415 A   7/1986  Luccio et al. ............... 378/119
4,891,521 A   1/1990  Danos .................... 250/370.09
6,285,028 B1  9/2001  Yamakawa ............. 250/370.09
6,414,317 B1  7/2002  Francke et al. .......... 250/385.1

FOREIGN PATENT DOCUMENTS

WO    WO 01/94979    12/2001

OTHER PUBLICATIONS

Search Report.

*Primary Examiner*—Edward J. Glick
*Assistant Examiner*—Courtney Thomas
(74) *Attorney, Agent, or Firm*—Harness, Dickey & Pierce, PLC

(57) ABSTRACT

A method for examining an object includes the steps of: producing ionizing radiation photons; providing other particles or photons, each of which carrying information regarding position, time, movement direction, and/or energy of a respective one of said ionizing radiation photons before having interacted with said object to be examined; detecting each of said other particles or photons to retrieve said information; having said ionizing radiation photons to interact with said object to be examined; detecting at least some of said ionizing radiation photons after having interacted with said object to retrieve information regarding position, time, movement direction, and/or energy of each of said detected ionizing radiation photons; correlating each of said detected ionizing radiation photons with a respective one of said other particles or photons; and deducing information of said examined object by means of said information as retrieved in the steps of detection.

39 Claims, 4 Drawing Sheets

METHOD AND AN APPARATUS FOR EXAMINING AN OBJECT BY USING IONIZING RADIATION

FIELD OF THE INVENTION

The invention relates to a method and an apparatus for examining an object by using ionizing radiation.

The invention may particularly be used in radiography, computerized tomography, and scattering tomography.

BACKGROUND OF THE INVENTION AND RELATED ART

Modern approaches of producing X-ray images and X-ray tomography use more and more advanced methods for detection of the photons, which pass through the object or which is scattered in the object. However, they have typically no or very little knowledge of the photons, which are entered into the object. At best, only some average properties of the incoming photon beam are known.

Such asymmetry of the measurements, i.e. when only one end (the output) of two ends of the process (input and output) is well-measured, is generally disadvantageous and leads inevitably to inefficiency and to restrictions in the choice of detecting methods.

A simple example of such an inefficient approach is when an object having both dense parts almost opaque to X-rays and thin well-transparent parts is imaged. The image of well-transparent parts has low contrast and large noise even if the number of photons detected by each picture element is large. This can be understood mathematically: the number of absorbed photons, which reflects the density of the object, is the difference of two large numbers close to each other, i.e. the unknown (fluctuating) number of incoming photons and the number of outgoing photons as being transmitted through the object.

SUMMARY OF THE INVENTION

If parameters of both the incoming and outgoing photons were individually detected and a simple anti-coincident electronics used, the number of absorbed photons would be counted directly with no error at all (or with a small error proportional to inefficiency of detector). The main source of the image noise will then be the quantum (random) character of the absorption process itself. It can easily be shown that this would improve the signal-to-noise ratio (S/N) of the image as much as 1/A times, where A is the absorption coefficient for the detected object.

A main object of the invention is therefore to provide a method and an apparatus for method for examining an object, which overcome the above-identified problems as being related with the prior art and which provide for measurements with an improved signal-to-noise ratio, particularly when examining objects or object regions which are highly transparent to the incident radiation, or which are strongly scattering the radiation.

In this respect there is a particular object to provide such a method and such an apparatus, which provide possibilities to detect photons before and after interaction with the object to be examined individually, and to correlate these detections to reveal more knowledge of the thickness, composition and/or density of the object.

A further object of the invention is to provide such a method and such an apparatus, which is suitable for high-quality measurements, e.g. in the fields of radiography, computerized tomography, and scattering tomography.

A still further object of the invention is to provide such a method and such an apparatus, which provide for excellent possibilities to develop new highly sophisticated applications.

These objects, among others, are attained by methods and apparatuses as claimed in the appended claims. These methods and apparatuses are based on different processes of creating tagged or labeled radiation photons, which in turn are used to reveal more information of the object examined than when using radiation photons from a conventional radiation source.

The present invention opens up for the development of a large number of high-accuracy applications in a variety of fields including medicine and non-destructive testing. Not at least applications based on scattered photons will be of great interest while employing the present invention.

Further, higher dose efficiency can be obtained and reconstruction ambiguities, which for instance conventional tomographic reconstructions from projections suffer from, can be avoided by use of information from scattered photons.

Further characteristics of the invention, and advantages thereof, will be evident from the detailed description of preferred embodiments of the present invention given hereinafter and the accompanying FIGS. 1–4, which are given by way of illustration only, and thus are not limitative of the present invention.

DESCRIPTION OF PREFERRED EMBODIMENTS

Figure 1:
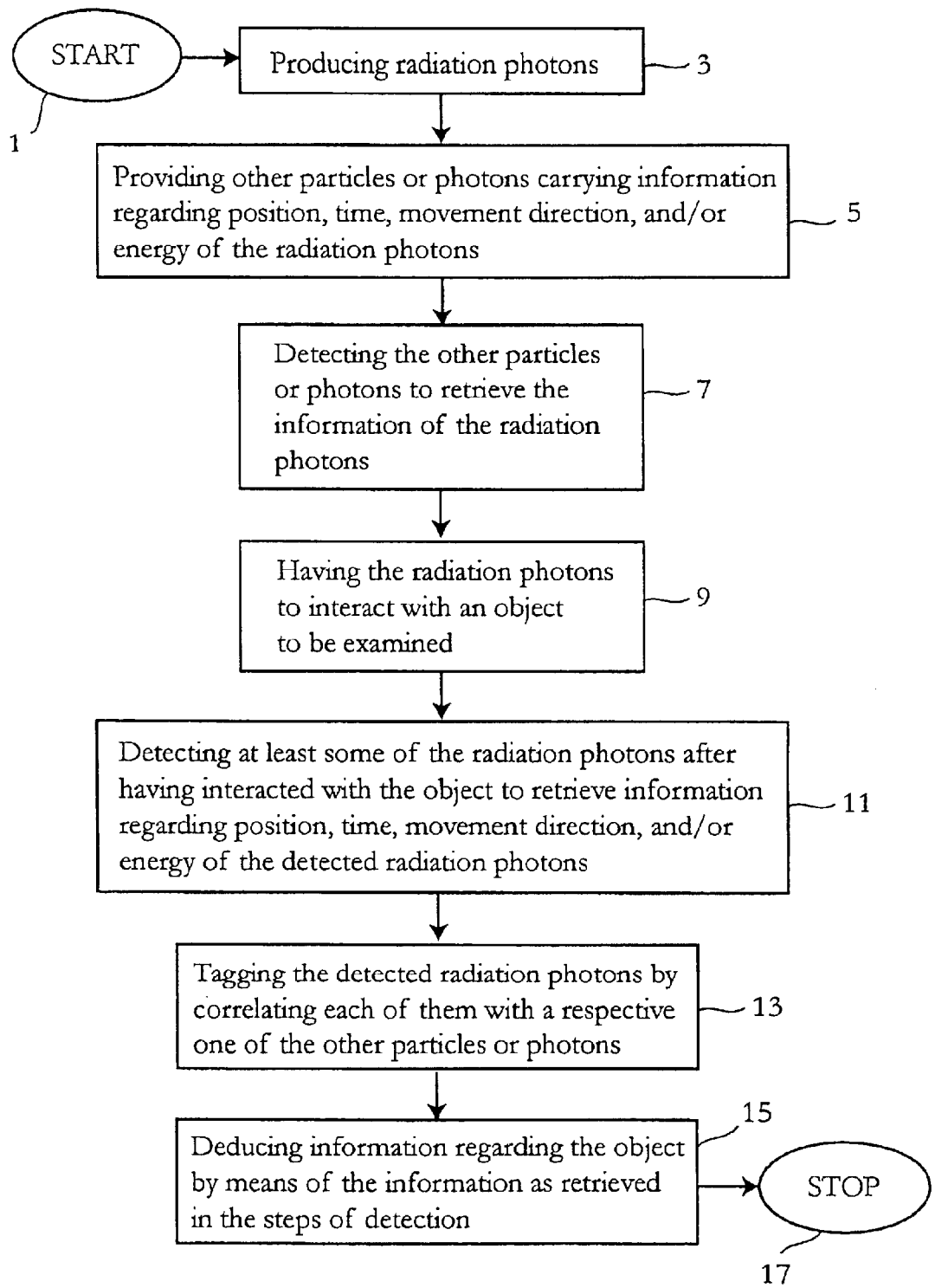
FIG. 1 illustrates in a schematic flow diagram a method for examining an object by means of ionizing radiation according to a preferred embodiment of the present invention.

An algorithm for examining an object by means of ionizing radiation according to a preferred embodiment of the present invention will be described below with reference to FIG. 1.

The algorithm is, in a step 1, started, and ionizing radiation photons to be irradiating an object to be examined are, in a step 3, produced. Three different cases can be distinguished: (i) the radiation photons may be produced by a synchrotron radiation source; (ii) the radiation photons may be produced by a conventional X-ray tube; or (iii) the radiation photons may be produced from radioactive isotopes.

Next, other particles or photons are provided in a step 5. These other particles or photons have participated in the production of the radiation photons produced in step 3 (case i), have been produced through interaction by the radiation photons produced in step 3 with matter (case ii), or have been produced simultaneously with the production of the radiation photons produced in step 3 (case iii). The other particles or photons may typically be electrons or X-ray or gamma photons. In either case each of the other particles or photons carries information regarding position at a given point of time, time of arrival at a given position, movement direction, and/or energy of a respective one of the radiation photons produced in step 3 before having interacted with the object to be examined.

Then, in a step 7, each of the other particles or photons is detected to retrieve the information of a respective one of the radiation photons produced in step 3. By such steps the radiation photons to be interacted with the object to be examined are tagged, i.e. marked, such that information is retrieved of each single photon, which is to interact with the object to be examined. The information may be concerned with position at a given point of time, time of arrival at a given position, movement direction, and/or energy of each of the photons.

This process of creating tagged radiation photons will for each of the three above-identified cases (i)–(iii) be described more in detail below with reference to FIGS. 2–4.

Before, simultaneously with, or subsequent to the detection of each of the other particles or photons, the radiation photons are, in a step 9, directed towards the object to be examined, and at least some of the radiation photons are, in a step 11, detected after having interacted with the object to be examined. Such detection is typically performed by detecting the existence of radiation photons at given positions and times. Alternatively, the detection can be seen as a registration of the absence of radiation photons at given positions and times.

This detection retrieves information regarding position at a given point of time, time of arrival at a given position, movement direction, and/or energy of each of the detected radiation photons. The radiation photons actually detected may be those who pass through the object without being deflected (one- and two-dimensional transmission tomography), or may be those who are scattered within a given angle (one-dimensional scattering tomography) or solid angle (two-dimensional scattering tomography). Other kind of measurement approaches may be utilized.

Note that the detector used for detection step 11 is preferably capable of single photon detection.

Next, each of the detected radiation photons is, in a step 13, matched or correlated with a respective one of the detected other particles or photons, i.e. each detected photon in step 11 is identified and is paired with the corresponding other particle or photon. Photons detected in step 11, which cannot be paired with corresponding other particles or photons are simply discarded.

Finally, in a step 15, information of the examined object is deduced by means of the information as retrieved in the steps of detection 7, 11, i.e. information of the photons before and after having interacted with the object. The algorithm is then, in a step 17, ended.

If the purpose of the examination is to perform transmission imaging or transmission tomography, it is sufficient to provide information of position at a given point of time, time of arrival at a given position and propagation direction of each radiation photon in step 7 and correlate this information with the respective detected photon to obtain the inventive concept of tagging. The knowledge of photon energy would improve the performance, but is not necessary.

If the purpose of the examination is to perform scattering tomography, it is also desirable to provide information of photon energy of each radiation photon. The accuracy and efficiency of the tomographic reconstruction is directly depending on the accuracy of the measurements of the photon parameters.

In an alternative version of the algorithm a correlation between each of the detected radiation photons with a respective one of the other particles or photons as detected is not actually needed. It is sufficient to know the number of the other particles or photons provided in step 5 and detected in step 7, and the ratio of the number of the other particles or photons provided in step 5 and the number of radiation photons produced in step 3 (for a given direction and period of time) in order to know the number of incident photons in a given direction during a given period of time. The ratio may be known from the kind of interaction between the radiation photons and the other particles or photons or determined by measurements.

Then, the number of radiation photons detected in step 11 is subtracted from the product of the number of the other particles or photons detected in step 7 and the ratio of the number of other particles or photons and the number of radiation photons. From this difference, and optionally from the number of incident radiation photons, information of the examined object is deduced.

If for instance the radiation photons, which actually are detected in step 11, are those who pass through the object without being deflected, the ratio of the difference and the number of incident radiation photons gives the transmission of the radiation photons through the object with extremely high accuracy and thus solves the problem as described on page 1, line 21—page 2, line 3 of the present description.

In yet an alternative version of the algorithm each of the other particles or photons carries information regarding position, direction and time of emission of a respective one of the radiation photons. Each of the other particles or photons is in step 7 detected to retrieve the information regarding position, direction and time of emission of the respective radiation photon. At least some of the radiation photons are in step 11 detected spatially and temporally resolved after having interacted with the object to retrieve information regarding detection position and time of the detected radiation photons. Finally, information regarding composition, structure or density of the examined object is deduced in step 15 by means of the information regarding position, direction and time of emission of the radiation photons, and position and time of the detected radiation photons.

The object to be examined may have thin parts, which are highly transparent to the radiation photons. Information regarding composition, structure or density of the examined object may be deduced by means of subtracting the number of detected radiation photons at each position from those emitted in a direction towards that position.

The source of the radiation photons can be a synchrotron radiation source, a conventional X-ray tube, or a radioactive isotope as identified above. All three sources can be used in all kind of detection apparatuses and imaging devices and the choice depends mostly on required energy, intensity, cost, etcetera.

Figure 2:
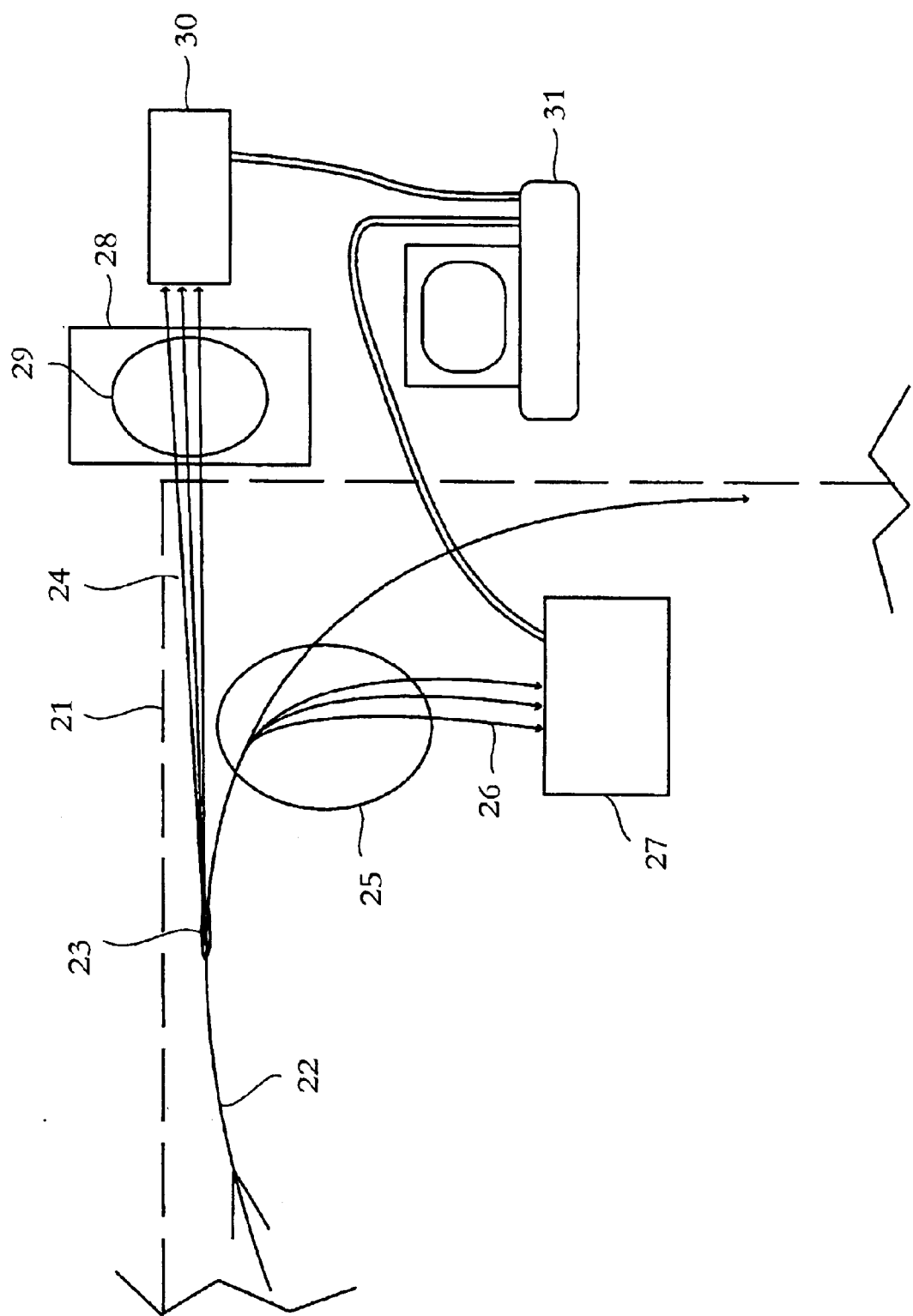
FIGS. 2–4 illustrate schematically detector apparatuses according to three preferred embodiments of the present invention.

In FIG. 2 is schematically illustrated a portion of a detector apparatus including a modified synchrotron radiation source according to a preferred embodiment of the present invention.

The synchrotron radiation source, a portion of which is schematically indicated by 21, includes an electron accelerator, which creates a circulating beam 22 of fast moving electrons. At a particular point along the electron beam 22 a device 23 for creating a localized strong magnetic field is arranged. The strong magnetic field causes the making electrons to wiggle in a transversal direction and to emit photons 24 in a narrow cone in a forward direction. Hereby, these electrons loose kinetic energy.

In a conventional synchrotron source measures are taken to compensate the energy loss of these electrons and to return them back to the circulating beam 22.

In this modified synchrotron source, however, the electron beam 22, after having passed the device 23, is entered into an electron separator 25, wherein electrons 26, which have lost some energy while emitting the photons 24, are easier deflected by an electromagnetic field than the rest of the beam and these electrons 26 are directed onto a first detector 27, which preferably is a time-resolved position sensitive electron detector. The degree of deflection corresponds to the energy of the emitted photons 24.

Further, an object area 28 for housing an object 29 to be examined is arranged in the path of the emitted photons 24, which will interact with the object 29. A second detector 30 is arranged to detect at least some of the emitted photons 24 after having interacted with the object 29.

If, on one hand, the second detector 30 is provided with a collimator in its front end, which is aligned with the incident photons 24, as is illustrated in FIG. 2, the photons, which pass through the object 29 without being deflected, will be detected. If, on the other hand, the second detector 30 is arranged in an angled position with respect to the incident photons 24, photons, which are scattered in the object 29, will be detected.

The second detector 30 is preferably a detector for time-resolved two-dimensional imaging, but other kind of detectors may be employed depending on the particular application.

The first and second detectors 27, 30 are connected to a signal-processing device 31 for post-analysis of the signals from the detectors 27, 30.

The first detector detects each electron time- and position-resolved to determine time of detection and kinetic energy of each electron. Time of emission and photon energy of the respective photon is deduced from time and position of detection of that electron. Point and direction of emission of each photon is typically given by the position of the device 23 for creating the localized strong magnetic field. The photons are emitted within a small volume and in a narrow cone in a forward direction with respect to the electrons.

The signal-processing device 31 correlates each of the radiation photons detected by detector 30 with a respective one of the electrons as detected by detector 27. Correlating each of the radiation photons detected by detector 30 with a respective one of the electrons may, at low fluxes, be performed by resolving the detections of the photons and electrons in time. At higher fluxes, the photon energy may be used for correlation (if detector 30 is provided with energy resolving capabilities). Once a photon is correlated with an electron information regarding time, point, direction and photon energy of the emission of that photon is known. Photons detected by detector 30, which cannot be correlated, are typically disregarded.

Finally, the signal-processing device 31 processes the information obtained and an image of the object is produced, the quality of which is superior to images produced using conventional detector apparatuses, or information of the object may be presented which is not possible to obtain using conventional detector apparatuses.

Figure 3:
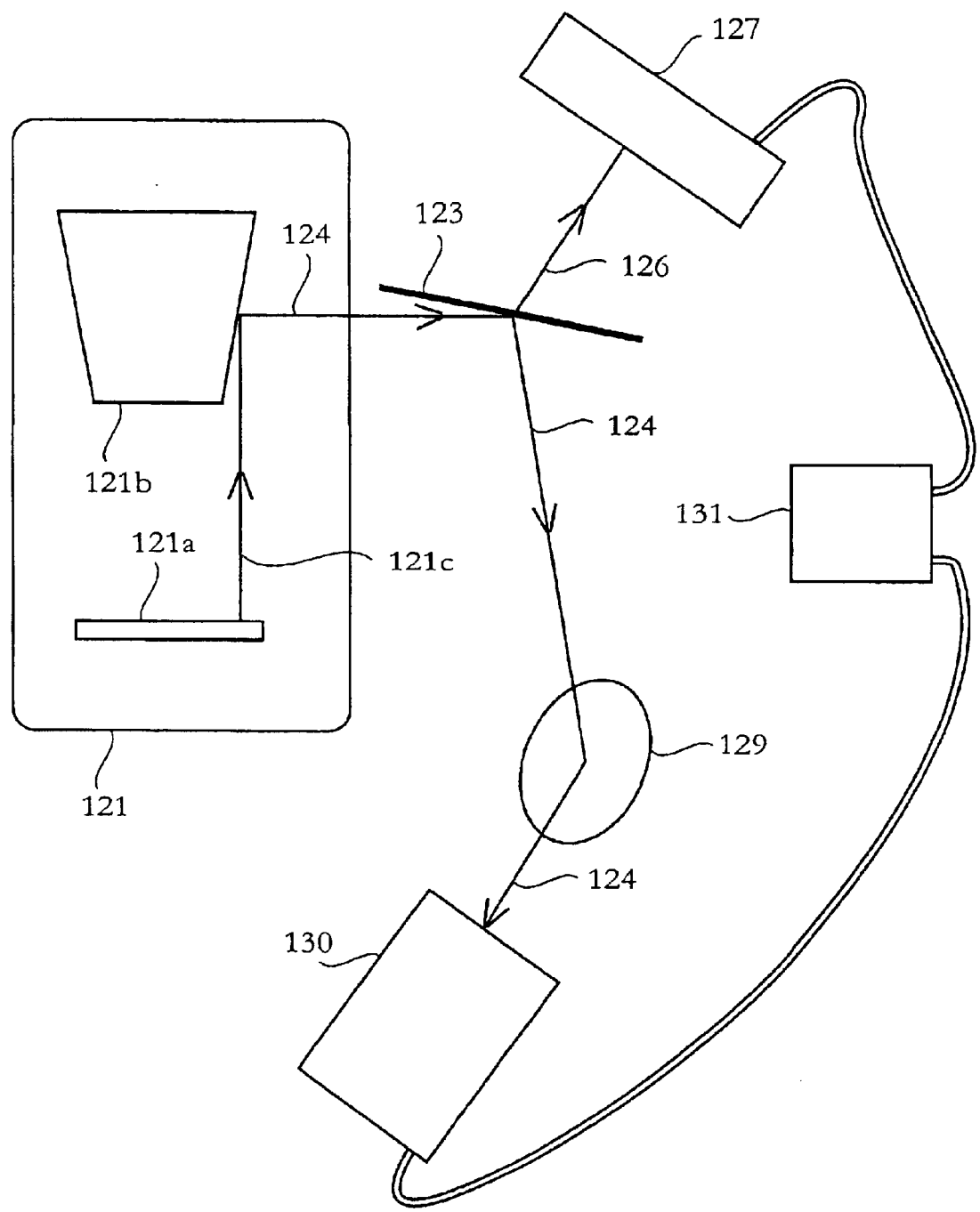

With reference next to FIG. 3, which schematically illustrates a detector apparatus based on a conventional X-ray tube as radiation source, a further preferred embodiment of the present invention will be described.

The main components of the FIG. 3 apparatus include an X-ray tube part 121, an X-ray photon scatterer 123, a position-sensitive electron detector 127, a position-sensitive X-ray photon detector 130, and signal-processing electronics 131.

The X-ray tube part 121, which may be any kind of X-ray tube known in the art, comprises typically a cathode 121a and an anode 121b, between which a high voltage is applied to accelerate electrons 121c emitted from the cathode towards the anode. X-rays 124 are emitted from the anode surface as a result of being hit by the electrons 121c, and a beam of these primary X-rays 124 is allowed to leave the X-ray tube part 121.

The beam of primary X-rays 124 is directed towards the X-ray photon scatterer 123, which typically consists of a metallic foil. The foil is preferably thin, e.g. about a few microns for aluminum and 50 kV X-rays. This implies that the efficiency of the use of the primary X-ray beam 124 in such an approach is low, but it may be increased if a multilayer structure is used instead of a single foil.

The beam of primary X-rays 124 are Compton scattered by the scatterer 123, and as a result of the interaction of the primary X-rays 124 with matter, electrons 126 are struck out and these recoil electrons 126 are detected by a position-sensitive electron detector 127. This detector is preferably capable of detecting the time, coordinate and energy of each of the recoil electrons 126 reaching the detector.

In an alternative version (not illustrated) the scatterer may be comprised in the position-sensitive electron detector. The scatterer may be comprised of a metallic entrance window of the detector or of a gas in case the detector is a gaseous-based detector.

By proper design of X-ray tube 121, scatterer 123, and electron detector 127, information regarding some or all of position at a given point of time, time of arrival at a given position, movement direction, and energy of individual ones of the Compton scattered X-ray photons 124 can be obtained.

An object 129 to be examined is placed in the path of the Compton scattered X-ray photons 124 and the position-sensitive X-ray photon detector 130 is arranged to detect some of the X-ray photons 124 scattered by the object 129 in a selected angle. Alternatively the detector 130 is arranged to detect the photons passing trough the object 129, without being deflected (not illustrated).

The detectors 127 and 130 are connected to the signal-processing electronics 131, which receives data from the detectors and processes the data to reveal information of the object 129.

Collimators and electromagnetic shields (not illustrated) are preferably placed between and around the X-ray tube 121, the scatterer 123, and the electron detector 127, and optionally other measures are taken, to reduce background from any X-ray photons scattered in the direction of the photon detector 130.

Regarding details of the detected parameters, correlation and processing by the electronics, and possible areas of application, reference is made to the description above of the embodiments of the invention illustrated in FIGS. 1–2.

Finally, with reference to FIG. 4, which schematically illustrates a detector apparatus using a radioactive isotope as radiation source, yet a further preferred embodiment of the present invention will be described.

Figure 4:
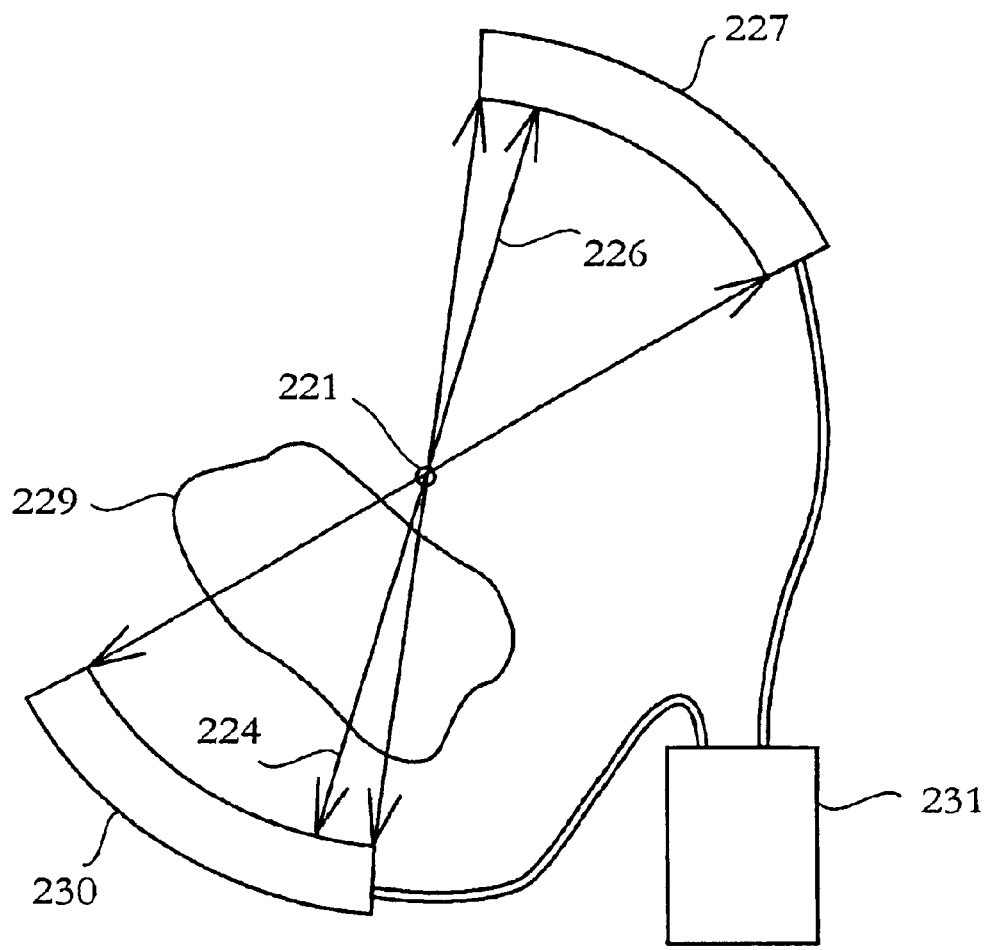

The main components of the FIG. 4 apparatus include a photon emitter 221, two position-sensitive detectors 227 and 230, and a signal-processing device 231.

The photon emitter 221, including a radioactive isotope, produces X-ray or gamma photons together with other particles or photons in a process, which involves a nuclear reaction.

One example of such photon emitter includes a positron emitting substance and a substance where said positron can be annihilated with an electron in a process producing two photons of identical energy simultaneously, which are emitted in opposite directions. The advantage of such photon source is that the point of emission is known a priori provided that the emitter is very small. Further, the photon energy is known.

A particular substance for the annihilation can be provided (not illustrated) or the annihilation can be obtained in the positron emitting substance itself.

One photon in each pair of co-emitted photons is detected by the detector 227, whereas an object to be examined is placed in the path of the other one in each pair of co-emitted photons. The second detector 230 is arranged to detect at least some of the photons, which have been transmitted through the object 229 without being deflected as being illustrated in FIG. 4. Alternatively, the second detector 230 detects photons scattered from the object 229 within some selected solid angle (not illustrated).

Preferably, the two detectors 227 and 230 are of the some kind and have capabilities of time-resolved two-dimensional imaging such that detector 227 is capable of establishing time and direction of emission for each photon detected (direction of emission is established from point of emission and position of detection), and that detector 230 is capable of recording time and position for detection of photons, which have interacted with the object 229. In an alternative version of the embodiment the two detectors are comprised of a single detector apparatus, e.g. any detector apparatus, which today is employed in PET tomography.

The two detectors 227 and 230 are connected to a signal-processing device 231 for processing of the data as recorded by the detectors.

Regarding details of the detected parameters, correlation and processing by the electronics, and possible areas of application, reference is made again to the description above of the embodiments of the invention illustrated in FIGS. 1–2.

To obtain an efficient tagging is a crucial issue in the present invention. Only some of the photons produced will be appropriately tagged, and of course only these photons will be used for the measurement of the object. The advantage of photon tagging according to the present invention is that the most simply identifiable tagging events may be distinguished and only photons tagged through these events are used in the measurement.

In the embodiment illustrated in FIG. 2 electrons that produce only one photon may be selected and thus only such produced photons are used for detection purposes. All other photons detected are discarded. In the embodiment illustrated in FIG. 3 only photons giving a single recoil electron may be selected. Other photons give a background, which can be either rejected, or used for getting complementary information about absorption in the object.

It will be obvious that the invention may be varied in a plurality of ways. Such variations are not to be regarded as a departure from the present invention.

What is claimed is:

1. A method for examining an object comprising the steps of:

producing ionizing radiation photons;

providing other particles or photons, said other particles or photons having participated in the production of said ionizing radiation photons, being produced through interaction of said ionizing radiation photons with matter, or being produced simultaneously with the production of said ionizing radiation photons; wherein each of said other particles or photons carries information regarding position at a given point of time, time of arrival at a given position, movement direction, and/or energy of a respective one of said ionizing radiation photons before having interacted with said object to be examined;

detecting each of said other particles or photons to retrieve said information of a respective one of said ionizing radiation photons before having interacted with said object to be examined;

causing said ionizing radiation photons to interact with said object to be examined;

detecting at least some of said ionizing radiation photons after having interacted with said object to be examined to retrieve information regarding position at a given point of time, time of arrival at a given position, movement direction, and/or energy of each of said detected ionizing radiation photons;

correlating each of said detected ionizing radiation photons with a respective one of said other particles or photons; and deducing information of said examined object by means of said information as retrieved in said steps of detection.

2. The method of claim 1 wherein said information regarding position at a given point of time, time of arrival at a given position, movement direction, and/or energy of a respective one of said ionizing radiation photons before having interacted with said object to be examined includes information regarding position at a given point of time, time of arrival at a given position, and movement direction of a respective one of said ionizing radiation photons before having interacted with said object to be examined; and said information regarding position at a given point of time, time of arrival at a given position, movement direction, and/or energy of each of said detected ionizing radiation photons includes information regarding position at a given point of time, time of arrival at a given position, and movement direction of each of said detected ionizing radiation photons.

3. The method of claim 2 wherein said information regarding position at a given point of time, time of arrival at a given position, movement direction, and/or energy of a respective one of said ionizing radiation photons before having interacted with said object to be examined includes also information regarding energy of a respective one of said ionizing radiation photons before having interacted with said object to be examined; and said information regarding position at a given point of time, time of arrival at a given position, movement direction, and/or energy of each of said detected ionizing radiation photons includes also information regarding energy of each of said detected ionizing radiation photons.

4. The method of claim 1 wherein said ionizing radiation photons are produced by a source of synchrotron radiation; and said other particles or photons are electrons from said source of synchrotron radiation, which have emitted said ionizing radiation photons while being accelerated in an electromagnetic field.

5. The method of claim 4 wherein said electrons are separated due to their energy-momentum by an electromagnetic separator, and subsequently detected.

6. The method of claim 5 wherein said electrons are separated due to their energy-momentum by an electromagnetic separator, and subsequently detected by a position-sensitive detector.

7. The method of claim 1 wherein
said ionizing radiation photons are produced by an X-ray tube; and
said other particles or photons are electrons released from a photon scatterer as a result of said ionizing radiation photons being scattered off said photon scatterer.

8. The method of claim 7 wherein said photon scatterer is comprised of a thin foil.

9. The method of claim 8 wherein said thin foil is a metallic foil.

10. The method of claim 9 wherein said metallic foil is an aluminum foil.

11. The method of claim 7 wherein said photon scatterer is comprised of a multilayer structure.

12. The method of claim 1 wherein said ionizing radiation photons and said other particles or photons are produced simultaneously pair by pair in a nuclear decay process.

13. The method of claim 1 wherein said ionizing radiation photons and said other particles or photons, which are photons, are produced simultaneously pair by pair in a reaction of electron-positron annihilation following the emission of positrons from a positron-emitting radioactive isotope.

14. The method of claim 1 wherein said ionizing radiation photons detected after having interacted with said object to be examined are substantially photons that are transmitted through said object without being absorbed or scattered.

15. The method of claim 14 wherein
each of said other particles or photons carries information regarding position, direction and time of emission of a respective one of said ionizing radiation photons;
each of said other particles or photons is detected to retrieve said information regarding position, direction and time of emission of a respective one of said ionizing radiation photons;
said at least some of said ionizing radiation photons are detected spatially and temporally resolved after having interacted with said object to retrieve information regarding detection position and time of each of said at least some of said ionizing radiation photons; and
information regarding composition, structure or density of said examined object is deduced by means of said information regarding position, direction and time of emission of said ionizing radiation photons, and position and time of said at least some of said ionizing radiation photons as detected after having interacted with said object.

16. The method of claim 15 wherein
said object to be examined has thin parts, which are highly transparent to said ionizing radiation photons,
information regarding composition, structure or density of said examined object is deduced by means of subtracting the number of ionizing radiation photons as detected at each position from those emitted in a direction towards said position.

17. The method of claim 1 wherein said ionizing radiation photons detected after having interacted with said object to be examined are substantially photons that are scattered in said object.

18. The method of claim 1 wherein
the step of detecting at least some of said ionizing radiation photons after having interacted with said object to be examined is performed by means of spatially resolved two dimensional imaging; and
the step of deducing information of said examined object by means of said information as retrieved in said steps of detection comprises to provide a two-dimensional image of said object.

19. A method for tomography including the method of claim 1.

20. An apparatus for examining an object comprising:
a source for producing ionizing radiation photons;
means for providing other particles or photons, said other particles or photons having participated in the production of said ionizing radiation photons, being produced through interaction of said ionizing radiation photons with matter, or being produced simultaneously with the production of said ionizing radiation photons; wherein each of said other particles or photons carries information regarding position at a given point of time, time of arrival at a given position, movement direction, and/or energy of a respective one of said ionizing radiation photons before having interacted with said object to be examined;
a first detector for detecting each of said other particles or photons to retrieve said information of a respective one of said ionizing radiation photons;
an object area for housing an object to be examined, the object area being arranged so that said ionizing radiation photons are directed to and interact with said object;
a second detector for detecting at least some of said ionizing radiation photons after having interacted with said object to be examined to retrieve information regarding position at a given point of time, time of arrival at a given position, movement direction, and/or energy of each of said detected ionizing radiation photons; and
a signal-processing device connected to said first and second detectors for correlating each of said detected ionizing radiation photons with a respective one of said other particles or photons, and for deducing information of said examined object by means of said information as retrieved by said first and second detectors.

21. The apparatus of claim 20 wherein
said information regarding position at a given point of time, time of arrival at a given position, movement direction, and/or energy of a respective one of said ionizing radiation photons before having interacted with said object to be examined includes information regarding position at a given point of time, time of arrival at a given position, and movement direction of a respective one of said ionizing radiation photons before having interacted with said object to be examined; and
said information regarding position at a given point of time, time of arrival at a given position, movement direction, and/or energy of each of said detected ionizing radiation photons includes information regarding position at a given point of time, time of arrival at a given position, and movement direction of each of said detected ionizing radiation photons.

22. The apparatus of claim 21 wherein
said information regarding position at a given point of time, time of arrival at a given position, movement direction, and/or energy of a respective one of said ionizing radiation photons before having interacted with said object to be examined includes also information regarding energy of a respective one of said ionizing radiation photons before having interacted with said object to be examined; and said information regarding position at a given point of time, time of arrival at a given position, movement direction, and/or energy of each of said detected ionizing radiation photons includes also information regarding energy of each of said detected ionizing radiation photons.

23. The apparatus of claim 20 wherein said source and said means for providing other particles or photons are comprised of a source of synchrotron radiation; and said other particles or photons are electrons from said source of synchrotron radiation, which have emitted said ionizing radiation photons while being accelerated in an electromagnetic field.

24. The apparatus of claim 20 further comprising an electromagnetic separator for separating said electrons due to their energy-momentum prior to being detected by said first detector.

25. The apparatus of claim 20 wherein said source is an X-ray tube; and said means for providing other particles or photons is a photon scatterer arranged to scatter said ionizing radiation photons and as a result thereof to release electrons.

26. The apparatus of claim 25 wherein said photon scatterer is comprised of a thin foil.

27. The apparatus of claim 26 wherein said thin foil is a metallic foil.

28. The apparatus of claim 27 wherein said metallic foil is an aluminum foil.

29. The apparatus of claim 25 wherein said photon scatterer is comprised of a multilayer structure.

30. The apparatus of claim 20 wherein said photon scatterer is comprised in said first detector for detecting each of said other particles or photons.

31. The apparatus of claim 20 wherein said source and said means for providing other particles or photons are comprised of a nuclear decaying substance, wherein said ionizing radiation photons and said other particles or photons are produced simultaneously pair by pair.

32. The apparatus of claim 20 wherein said source and said means for providing other particles or photons are comprised of a radioactive isotope emitting positrons and a substance for electron-positron annihilation emitting said ionizing radiation photons and said other particles or photons, which are photons, simultaneously pair by pair.

33. The apparatus of claim 20 wherein said second detector is arranged to detect ionizing radiation photons that are transmitted through said object without being absorbed or scattered.

34. The apparatus of claim 33 wherein said first detector is adapted to detect each of said other particles or photons to retrieve information regarding position, direction and time of emission of a respective one of said ionizing radiation photons;

said second detector is adapted to detect said at least some of said ionizing radiation photons after having interacted with said object to be examined spatially and temporally resolved to retrieve information regarding detection position and time of each of said detected ionizing radiation photons;

said signal-processing device is adapted to deduce information regarding composition, structure or density of said examined object by means of subtracting the number of ionizing radiation photons as detected at each position from those emitted in a direction towards said position.

35. The apparatus of claim 20 wherein said second detector is arranged to detect ionizing radiation photons that are scattered in said object.

36. The apparatus of claim 20 wherein said second detector is a two dimensional detector for spatially resolved two dimensional imaging; and said signal-processing device is adapted to provide a two-dimensional image of said object by means of said information as retrieved by said first and second detectors.

37. A method for examining an object comprising the steps of:

producing ionizing radiation photons;

providing other particles or photons, said other particles or photons having participated in the production of said ionizing radiation photons, being produced through interaction by said ionizing radiation photons with matter, or being produced simultaneously with the production of said ionizing radiation photons, wherein a ratio of a number of said other particles or photons and a number of ionizing radiation photons is known;

detecting each of said other particles or photons;

having said ionizing radiation photons to interact with said object to be examined;

detecting at least some of said ionizing radiation photons after having interacted with said object to be examined;

subtracting the number of said detected ionizing radiation photons from the product of the number of said detected other particles or photons and the ratio of the number of said other particles or photons and the number of ionizing radiation photons; and deducing information of said examined object by means of said difference.

38. The method of claim 37 wherein said at least some of said ionizing radiation photons detected after having interacted with said object to be examined are propagating in paths being essentially parallel with, and close to, each other.

39. An apparatus for examining an object comprising:

a source for producing ionizing radiation photons;

means for providing other particles or photons, said other particles or photons having participated in the production of said ionizing radiation photons, being produced through interaction by said ionizing radiation photons with matter, or being produced simultaneously with the production of said ionizing radiation photons, wherein a ratio of a number of said other particles or photons and a number of ionizing radiation photons is known;

a first detector detecting each of said other particles or photons;

an object area for housing an object to be examined, the object area being arranged so that said ionizing radiation photons are directed to and interacting with said object;

a second detector for detecting at least some of said ionizing radiation photons after having interacted with said object to be examined;

a signal-processing device connected to said first and second detectors for subtracting the number of said detected ionizing radiation photons from the product of the number of said detected other particles or photons and the ratio of the number of said other particles or photons and the number of ionizing radiation photons, and for deducing information of said examined object by means of said difference.

* * * * *